United States Patent
Ashton et al.

(10) Patent No.: US 11,490,956 B2
(45) Date of Patent: *Nov. 8, 2022

(54) CATHETER UTILIZING OPTICAL SPECTROSCOPY FOR MEASURING TISSUE CONTACT AREA

(71) Applicant: BIOSENSE WEBSTER (ISRAEL) LTD., Yokneam (IL)

(72) Inventors: John H. Ashton, Glendora, CA (US); Jeffrey L. Clark, Castaic, CA (US); George Kamin, Arcadia, CA (US); Joseph Keyes, Sierra Madre, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 824 days.

This patent is subject to a terminal disclaimer.

(21) Appl. No.: 16/402,685

(22) Filed: May 3, 2019

(65) Prior Publication Data

US 2019/0254742 A1 Aug. 22, 2019

Related U.S. Application Data

(63) Continuation of application No. 14/145,858, filed on Dec. 31, 2013, now Pat. No. 10,278,775.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0084* (2013.01); *A61B 5/6855* (2013.01);
(Continued)

(58) Field of Classification Search
CPC ........ A61B 2018/1405; A61B 18/1492; A61B 5/0075
See application file for complete search history.

(56) References Cited

U.S. PATENT DOCUMENTS

| 4,669,467 A | 6/1987 | Willett et al. |
| 4,718,417 A | 1/1988 | Kittrell et al. |

(Continued)

FOREIGN PATENT DOCUMENTS

| CN | 101332120 A | 12/2008 |
| CN | 101617957 A | 1/2010 |

(Continued)

OTHER PUBLICATIONS

Extended European Search Report for European Application No. 14200527.1, dated May 6, 2015, 6 pages.

(Continued)

*Primary Examiner* — Eun Hwa Kim
(74) *Attorney, Agent, or Firm* — Etan S. Chatlynne; Calderon Safran & Cole, P.C.

(57) ABSTRACT

A catheter comprises an elongated catheter body, a control handle, and a hollow tip electrode having a radially-symmetrical shell defining a cavity surrounding a center inner location from which light is emitted to pass through a plurality of openings formed in the shell for interaction with tissue and/or fluid, such as blood, outside of and in contact with the shell. Light interacting with tissue is reflected back into the cavity for collection whereas light interacting with fluid, such as blood, is absorbed. By analyzing the light collected in the cavity, a determination is made as to a ratio of light reflected by tissue versus light absorbed by fluid for indicating the amount of contact between the tip electrode and tissue. Alternatively, fluorescence may similarly be employed (light is emitted at one wavelength and detected at one or more different wavelengths) since tissue and blood have different fluorescence properties at various wavelengths. An integrated ablation and spectroscopy system further comprises an RF generator, a light source and a light analyzer adapted to analyze the light collected in the cavity.

17 Claims, 11 Drawing Sheets

(51) Int. Cl.
*A61B 17/00* (2006.01)
*A61B 18/00* (2006.01)
*A61B 90/00* (2016.01)
*A61B 90/30* (2016.01)

(52) U.S. Cl.
CPC ............... *A61B 2017/00057* (2013.01); *A61B 2017/00061* (2013.01); *A61B 2018/00351* (2013.01); *A61B 2018/00642* (2013.01); *A61B 2090/306* (2016.02); *A61B 2090/3614* (2016.02); *A61B 2218/002* (2013.01)

(56) References Cited

U.S. PATENT DOCUMENTS

| | | |
|---|---|---|
| 4,781,417 A | 11/1988 | Shipman et al. |
| RE34,502 E | 1/1994 | Webster, Jr. |
| 5,391,199 A | 2/1995 | Ben-Haim |
| 5,443,489 A | 8/1995 | Ben-Haim |
| 5,480,422 A | 1/1996 | Ben-Haim |
| 5,537,686 A | 7/1996 | Krutz, Jr. et al. |
| 5,546,951 A | 8/1996 | Ben-Haim |
| 5,558,091 A | 9/1996 | Acker et al. |
| 5,568,809 A | 10/1996 | Ben-Haim |
| 5,897,529 A | 4/1999 | Ponzi |
| 6,024,739 A | 2/2000 | Ponzi et al. |
| 6,123,699 A | 9/2000 | Webster, Jr. |
| 6,171,277 B1 | 1/2001 | Ponzi |
| 6,179,835 B1 | 1/2001 | Panescu et al. |
| 6,183,463 B1 | 2/2001 | Webster, Jr. |
| 6,264,653 B1 | 7/2001 | Falwell |
| 6,377,841 B1 | 4/2002 | Lin et al. |
| 6,508,765 B2 | 1/2003 | Suorsa et al. |
| 6,575,931 B1 | 6/2003 | Ponzi |
| 6,992,477 B2 | 1/2006 | Govari |
| 7,194,294 B2 | 3/2007 | Panescu et al. |
| 7,591,816 B2 | 9/2009 | Wang et al. |
| 7,623,906 B2 | 11/2009 | Robinson et al. |
| 7,727,231 B2 | 6/2010 | Swanson |
| 7,952,719 B2 | 5/2011 | Brennan, III |
| 8,265,745 B2 | 9/2012 | Hauck et al. |
| 8,267,926 B2 | 9/2012 | Paul et al. |
| 9,882,125 B2 | 1/2018 | Toh et al. |
| 2007/0106287 A1 | 5/2007 | O'Sullivan |
| 2007/0106289 A1 | 5/2007 | O'Sullivan |
| 2007/0287998 A1 | 12/2007 | Sharareh et al. |
| 2008/0097220 A1 | 4/2008 | Lieber et al. |
| 2008/0119694 A1 | 5/2008 | Lee |
| 2009/0005768 A1 | 1/2009 | Sharareh et al. |
| 2009/0005771 A1 | 1/2009 | Lieber et al. |
| 2009/0005773 A1 | 1/2009 | Beeckler et al. |
| 2009/0131931 A1 | 5/2009 | Lee et al. |
| 2011/0118735 A1 | 5/2011 | Abou-Marie et al. |
| 2012/0265184 A1 | 10/2012 | Sliwa et al. |

FOREIGN PATENT DOCUMENTS

| | | |
|---|---|---|
| EP | 2008603 A1 | 12/2008 |
| EP | 2062545 A2 | 5/2009 |
| JP | 2009056289 A | 3/2009 |
| JP | 2009148550 A | 7/2009 |
| WO | 9502995 A1 | 2/1995 |
| WO | 9605768 A1 | 2/1996 |
| WO | 9724983 A2 | 7/1997 |
| WO | 9829033 A1 | 7/1998 |

OTHER PUBLICATIONS

Extended European Search Report for European Application No. 18174951.6, dated Jul. 4, 2018, 7 pages.
Office Action for European Application No. 14200527.1, dated Dec. 1, 2016, 4 pages.
Venius J., et al., "Visualization of Human Heart Conduction System by Means of Fluorescence Spectroscopy," Journal of Biomedical Optics, Oct. 2011, vol. 16 (10), pp. 107001-1-107001-9.

PRIOR ART

CATHETER UTILIZING OPTICAL SPECTROSCOPY FOR MEASURING TISSUE CONTACT AREA

CROSS REFERENCE TO RELATED APPLICATION

The present application is a Continuation under 35 U.S.C. § 120 of U.S. patent application Ser. No. 14/145,858, filed Dec. 31, 2013. The entire contents of this application is incorporated by reference herein in its entirety.

FIELD OF INVENTION

This invention relates to catheters, in particular, cardiac catheters for ablation and tissue diagnostics.

BACKGROUND

Radiofrequency (RF) ablation of cardiac and other tissue is a well-known method for creating thermal injury lesions at the tip of an electrode. Radiofrequency current is delivered between a skin (ground) patch and the electrode. Electrical resistance at the electrode-tissue interface results in direct resistive heating of a small area, the size of which depends upon the size of the electrode, electrode tissue contact, and current (density). Further tissue heating results from conduction of heat within the tissue to a larger zone. Tissue heated beyond a threshold of approximately 50-55 degrees C. is irreversibly injured (ablated).

Resistive heating is caused by energy absorption due to electrical resistance. Energy absorption is related to the square of current density and inversely with tissue conductivity. Current density varies with contact area conductivity, voltage and inversely with the square of radius from the ablating electrode. Therefore, energy absorption varies with conductivity, the square of applied voltage, and inversely with the fourth power of radius from the electrode. Resistive heating, therefore, is most heavily influenced by radius, and penetrates a very small distance from the ablating electrode. The rest of the lesion is created by thermal conduction from the area of resistive heating. This imposes a limit on the size of ablation lesions that can be delivered from a surface electrode.

Theoretical methods to increase lesion size would include increasing electrode diameter, increasing the area of electrode contact with tissue, increasing tissue conductivity and penetrating the tissue to achieve greater depth and increase the area of contact, and delivering RF until maximal lesion size has been achieved (60-90 seconds for full maturation).

The electrode can be introduced to the tissue of interest directly (for superficial/skin structures), surgically, endoscopically, laparoscopically or using percutaneous transvascular (catheter-based) access. Catheter ablation is a well-described and commonly performed method by which many cardiac arrhythmias are treated.

Catheter ablation is sometimes limited by insufficient lesion size. Ablation of tissue from an endovascular approach results not only in heating of tissue, but heating of the electrode. When the electrode reaches critical temperatures, denaturation of blood proteins causes coagulum formation. Impedance can then rise and limit current delivery. Within tissue, overheating can cause steam bubble formation (steam "pops") with risk of uncontrolled tissue destruction or undesirable perforation of bodily structures. In cardiac ablation, clinical success is sometimes hampered by inadequate lesion depth and transverse diameter even when using catheters with active cooling of the tip. Theoretical solutions have included increasing the electrode size (increasing contact surface and increasing convective cooling by blood flow), improving electrode-tissue contact, actively cooling the electrode with fluid infusion, changing the material composition of the electrode to improve current delivery to tissue, and pulsing current delivery to allow intermittent cooling.

To improve electrode-tissue contact, current catheters may have pressure sensors at the distal tip to detect whether the tip electrode is in contact with tissue. However, merely detecting contact does not indicate how much of the tip electrode is actually surrounded by tissue or by fluid and blood. Introduction of an energized electrode into cardiac space results in the formation of a simplified resistive circuit; current flows from the electrode through two parallel resistors via the surrounding blood and the contacting tissue. Understanding the relative surface area of each of these paths will allow for an estimation of each path's respective resistance and therefore the current flow. Such information would be helpful to improve estimation of size and shape of lesions created by ablation, as lesion size and shape are likely a function of power, time and size of contact area of electrode and tissue.

Method and apparatus employing optical spectroscopy for determining tissue attributes are known. For example, U.S. Pat. No. 7,623,906 discloses a method and an apparatus for a diffuse reflectance spectroscopy which includes a specular control device that permits a spectroscopic analyzer to receive diffusely reflected light reflected from tissue. U.S. Pat. No. 7,952,719 discloses an optical catheter configuration combining Raman spectroscopy with optical fiber-based low coherence reflectometry. U.S. Pat. No. 6,377,841 discloses the use of optical spectrometry for brain tumor demarcation.

Accordingly, it is desirable that a catheter be able to assess and measure the amount of contact between an ablation electrode and tissue versus fluid, such as blood, for improving lesion size and depth. It is also desirable that the catheter effectuate such assessment and measurement by optical means that can measure accurately and fit inside the tip electrode without disruption to the function of the tip electrode.

SUMMARY OF THE INVENTION

The present invention is directed to a catheter with an irrigated distal tip ablation electrode adapted to assess and measure the extent of contact between the ablation electrode and surrounding tissue. The catheter comprises an elongated catheter shaft, a control handle, and a distal tip electrode having a thin shell with a radially-symmetrical portion defining a cavity. The tip electrode has one or more light emitters configured to emit light from a first predetermined location in the cavity and one or more light detectors configured to collect light from a second predetermined location in the cavity, where the second predetermined location may or may not be generally identical to the first predetermined location. In accordance with a feature of the invention, the light is radiated from the first predetermined location toward the shell where it reflects off the inner surface of the shell or it passes through apertures formed in the shell and interacts with matter(s) outside of the tip electrode. Depending on the interactions of the light with the matter(s) encountered outside of the apertures, the light inside the cavity as collected by the one or more collector waveguides is analyzed to provide an indication of the matter(s) encountered, including, for example, the nature of the matter(s), the amount of the matter(s) and/or the position or orientation of the matter(s) relative to the tip electrode, where the matter(s) may include, for example, tissue and fluid, such as blood. The indication may be used in selective energization of the tip electrode for ablating tissue. In one embodiment, the light received by the light detector is analyzed to determine a ratio of light reflected by tissue versus light absorbed by fluid for indicating the amount of contact between the tip electrode and tissue.

Figure 8:
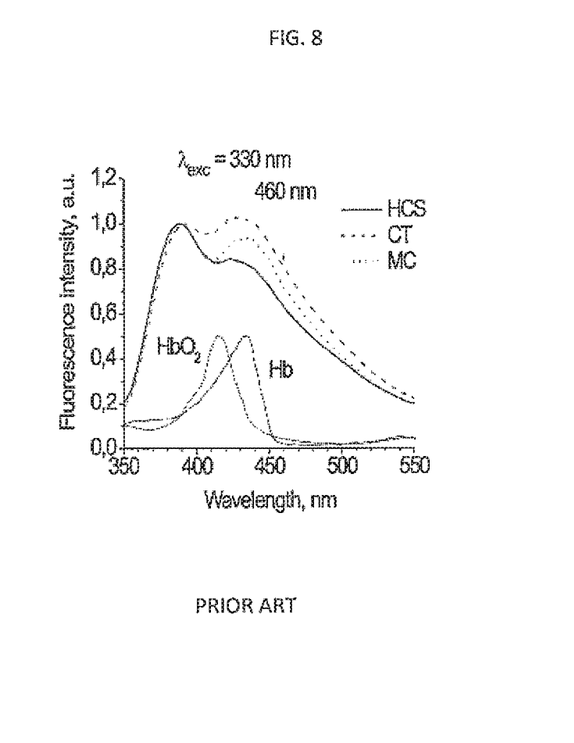
FIG. 8 is a fluorescence spectra of HCS (heart conduction system), CT (connective tissue) and MC (myocardium) normalized to the first band (at 390 nm). The normalized absorption spectra of oxyhemoglobin HbO2 and hemoglobin Hb are also added. Venius, J., et al., J. Biomed. Opt. 16(10) 2011.

Alternatively, fluorescence may similarly be employed instead of basic light reflectance. During fluorescence, light may be emitted by the catheter at one wavelength and absorbed by the tissue or blood. As a result of the energy absorbed, the tissue or blood then emits lights back at a different wavelength, and the catheter detects the amount or intensity of light at this other wavelength. Tissue and blood have different fluorescence properties at various wavelengths, and this difference can be also utilized to determine what ratio of the tip is contacting tissue versus blood. For example, it has been shown that at an excitation wavelength of 330 nm, myocardium (in cardiac tissue) fluoresces more than hemoglobin (in blood) in the range of 350-550 nm, with a peak difference at about 390 nm (see FIG. 8). Venius, J., et al., J. Biomed. Opt. 16(10) 2011.

The present invention includes an integrated catheter-based ablation and spectroscopy system having the aforementioned catheter, an RF generator for providing RF energy to the tip electrode assembly, a light source to provide light energy, and an optical analyzer, for example, a spectrometer, to detect and analyze optical data collected by the one or more collector wave guides. In that regard, it is understood that the spectrometer is any instrument used to probe a property of light as a function of its portion of the electromagnetic spectrum, typically its wavelength, frequency, or energy. The property being measured is often, but not limited to, intensity of light, but other variables like polarization can also be measured. Technically, a spectrometer can function over any range of light, but most operate in a particular region of the electromagnetic spectrum.

The system may also include a patient interface unit and a communication (COM) unit, a processor and a display, where the COM unit provides electronics for ECG, electrogram collection, amplification, filtering and real-time tracing of catheter distal tip and the PIU allows communication with various components of the system, including signal generator, recording devices, etc. The system may include a location pad with magnetic field generators (e.g., coils) to generate magnetic fields within the patient's body. Signals detected by a sensor housed in the catheter in response to the magnetic fields are processed by the processor order to determine the position (location and/or orientation) coordinates of the catheter distal end. Other signals from the catheter, for example, tissue electrical activity and temperature, are also collected by the catheter and transmitted to the COM unit and the processor via the PIU for processing and analysis.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
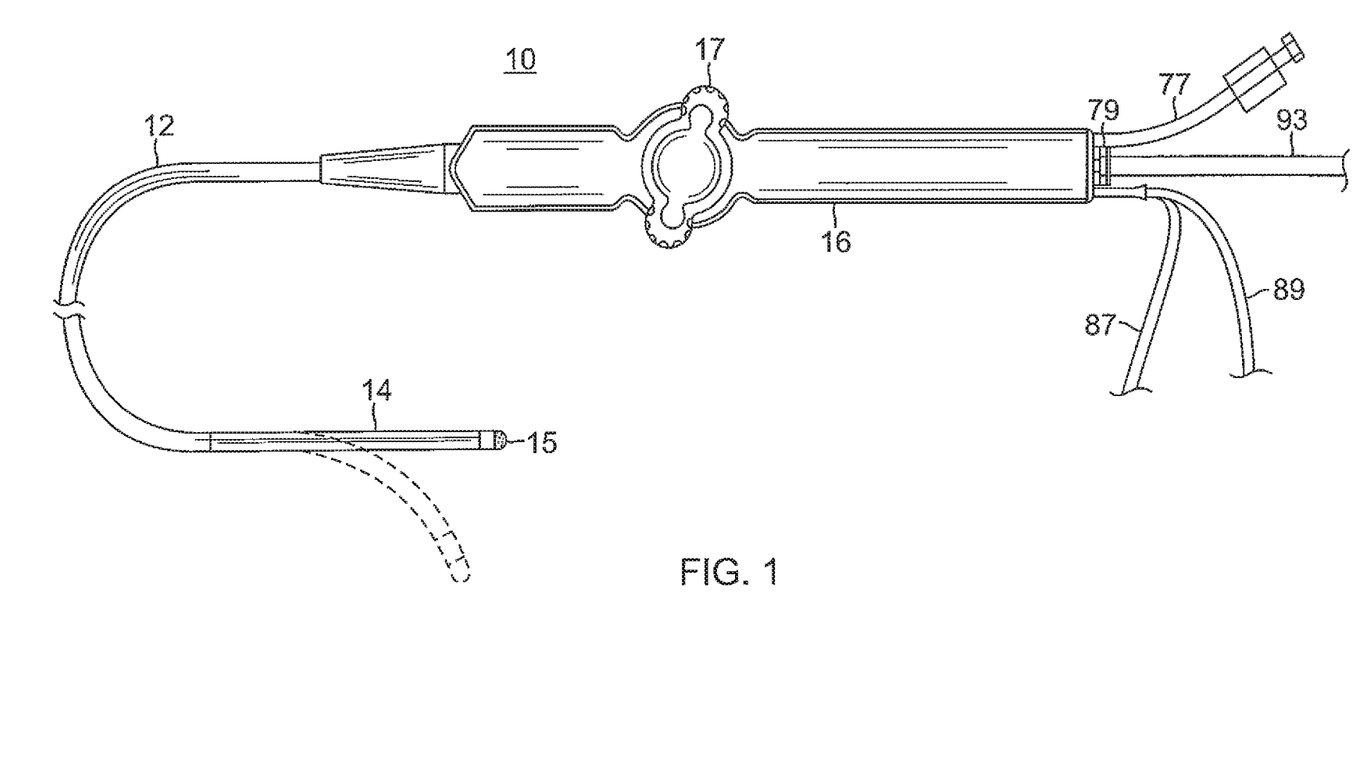
FIG. 1 is a perspective view of a catheter of the present invention, in accordance with one embodiment.

As shown in FIG. 1, the catheter 10 comprises an elongated catheter body 12, deflectable intermediate section 14, a distal tip electrode 15 and a deflection control handle 16 attached to the proximal end of the catheter body 12. As described further below, the distal tip electrode 15 is adapted to provide optically-based indications of matter surrounding the tip electrode, including for example, the degree to which the tip electrode is surrounded by or in contact with soft tissue, versus fluid, such as blood.

Figure 2A:
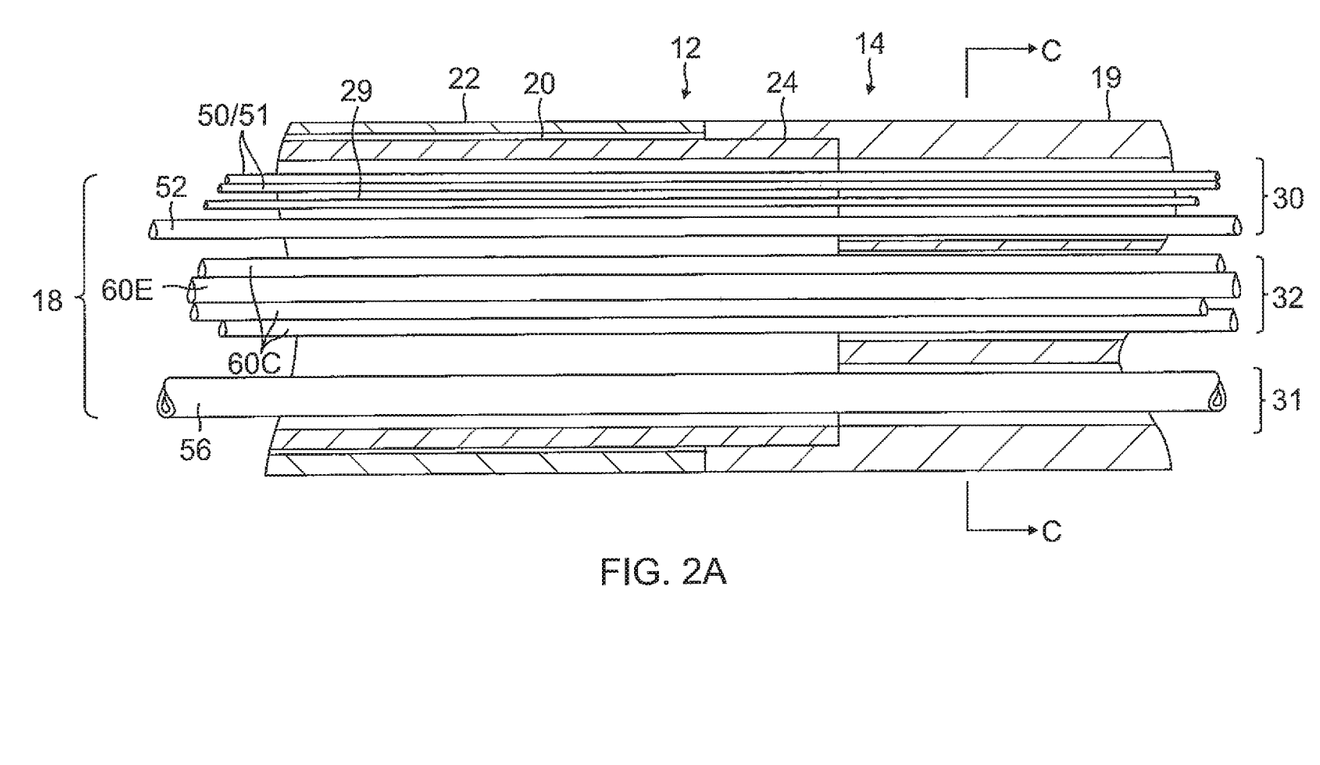
FIG. 2A is a side cross-sectional view of the catheter of FIG. 1, including a junction between a catheter body and a deflectable intermediate section, along a first diameter.
Figure 2B:
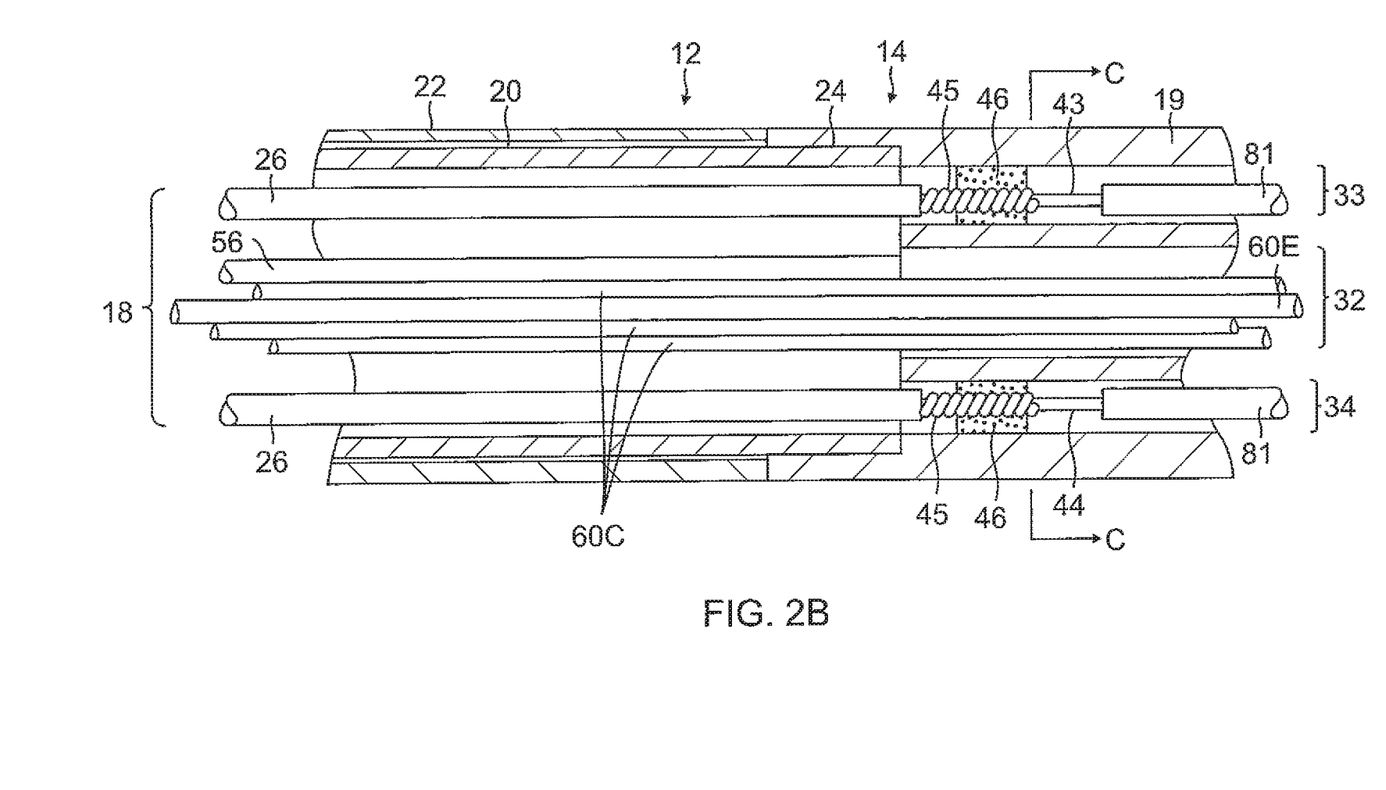
FIG. 2B is a side cross-sectional view of the catheter of FIG. 1, including a junction between a catheter body and a deflectable intermediate section, along a second diameter generally perpendicular to the first diameter of FIG. 2A.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. A presently preferred construction comprises an outer wall 22 made of polyurethane or nylon. The outer wall 22 comprises an imbedded braided mesh of stainless steel or the like to increase torsional stiffness of the catheter body 12 so that, when the deflection control handle 16 is rotated, the intermediate section 14 of the catheter 10 will rotate in a corresponding manner.

The outer diameter of the catheter body 12 is not critical, but is preferably no more than about 8 French. Likewise the thickness of the outer wall 22 is not critical. In the depicted embodiment, the inner surface of the outer wall 22 is lined with a stiffening tube 20, which can be made of any suitable material, preferably polyimide. The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22.

Figure 2C:
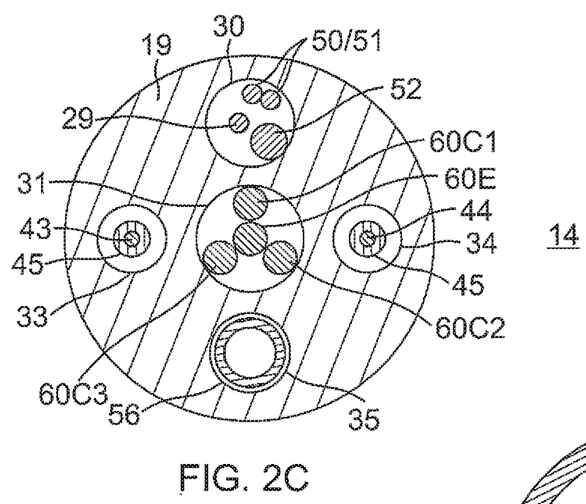
FIG. 2C is an end cross-sectional view of the deflectable intermediate section of FIGS. 2A and 2B, taken along line C-C.

As shown in FIGS. 2A, 2B and 2C, the intermediate section 14 comprises a short section of multi-lumened tubing 19 having, for example, at least four lumens, namely a first lumen 30, a second lumen 31, a third lumen 32, a fourth off-axis puller wire lumen 33 for uni-directional deflection, and a fifth off-axis lumen 34 diametrically opposite of lumen 33 for bidirectional deflection. The tubing 19 is made of a suitable non-toxic material that is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French.

A suitable means for attaching the catheter body 12 to the intermediate section 14 is illustrated in FIGS. 2A and 2B. The proximal end of the intermediate section 14 comprises an inner counter bore 24 that receives the outer surface of the stiffener 20. The intermediate section 14 and catheter body 12 are attached by glue or the like. Other methods for attaching can be used in accordance with the invention.

The stiffening tube 20 is held in place relative to the outer wall 22 at the catheter body 12. In a suitable construction of the catheter body 12, a force is applied to the proximal end of the stiffening tube 20, which causes the distal end of the stiffening tube 20 to firmly push against the counter bore 24. While under compression, a first glue joint is made between the stiffening tube 20 and the outer wall 22 by a fast drying glue, e.g. Super Glue®. Thereafter, a second glue joint is formed between the proximal ends of the stiffening tube 20 and outer wall 22 using a slower drying but stronger glue, e.g., polyurethane.

Extending from the control handle 16 and through the center lumen 18 of the catheter body 12 and the first lumen 30 of the tubing 19 are a lead wire 29 for the tip electrode 15, a thermocouple wire pair 50 and 51 for sensing temperature of the tip electrode, and a cable 52 for an electromagnetic location sensor 54 housed near the tip electrode 15. Extending from the control handle 16 and through the center lumen 18 and the second lumen 31 is an irrigation tubing 56 for passing fluid, e.g., saline, from the control handle 16 and along the length of the catheter to the tip electrode 15. Extending from the control handle 16 and through the center lumen 18 and the third lumen 32 is at least two optical waveguides, for example, an emitter waveguide 60E and a collector waveguide 60C. In the disclosed embodiment, there are one emitter waveguide and three collector waveguides.

The depicted catheter includes a mechanism for deflecting the catheter body 12. In the depicted embodiment, the catheter is adapted for bi-directional deflection with a first puller wire 43 extending into the puller wire lumen 33 and a second puller wire 44 extending into the puller wire lumen 34. The puller wires 43 and 44 are anchored at their proximal ends in the deflection control handle 16 and anchored at their distal end at or near a distal end of the intermediate section 14. The puller wires are made of any suitable metal, such as stainless steel or Nitinol, and are preferably coated with Teflon® or the like. The coating imparts lubricity to the puller wires. Each puller wire preferably has a diameter ranging from about 0.006 to about 0.010 inches.

To effectuate deflection of the intermediate section 14, each puller wire is surrounded by a respective compression coil 45 that extends from the proximal end of the catheter body 12 and terminates at or near the proximal end of the intermediate section 14. Each compression coil 45 is made of any suitable metal, preferably stainless steel. The compression coil 45 is tightly wound on itself to provide flexibility, i.e., bending, but to resist compression. The inner diameter of the compression coil 45 is preferably slightly larger than the diameter of the puller wire. For example, when the puller wire has a diameter of about 0.007 inches, the compression coil preferably has an inner diameter of about 0.008 inches. The Teflon® coating on the puller wire allows it to slide freely within the compression coil 45. Along its length, the outer surface of each compression coil 45 is covered by a respective flexible, non-conductive sheath 26 to prevent contact between the compression coils and any other components inside the catheter body 12. The non-conductive sheath 26 may be made of polyimide tubing. Each compression coil 45 is anchored at its proximal end to the proximal end of the stiffening tube 20 in the catheter body 12 by glue (not shown). At its distal end, each compression coil is anchored in the respective puller wire lumen 33 and 34 by glue joint 46 (FIG. 2B). Within the intermediate section 14, the puller wires 43 and 44 extend through a respective protective sheath 81, for example of Teflon®, which prevents the puller wire from cutting into the wall of the tubing 19 when the section 14 is deflected.

Figure 4A:
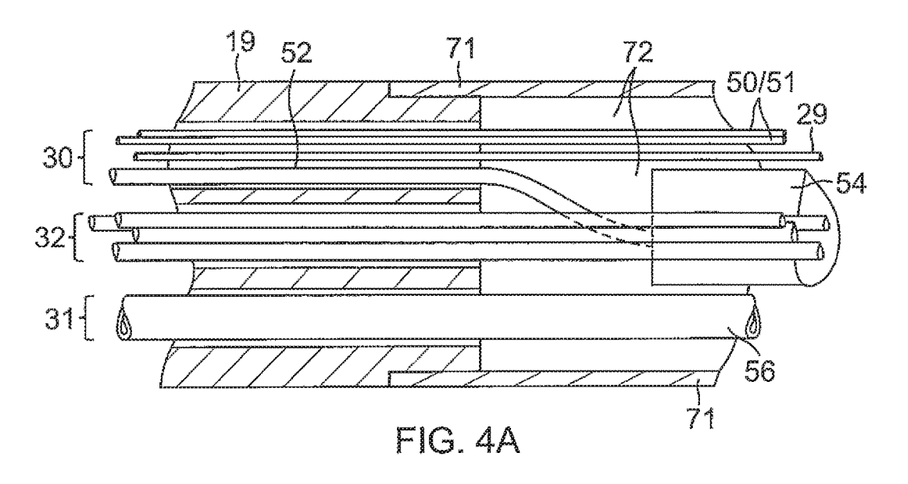
FIG. 4A is a side cross-sectional view of a junction between a deflectable intermediate section and a connector member, in accordance with one embodiment, taken along a first diameter.
Figure 4B:
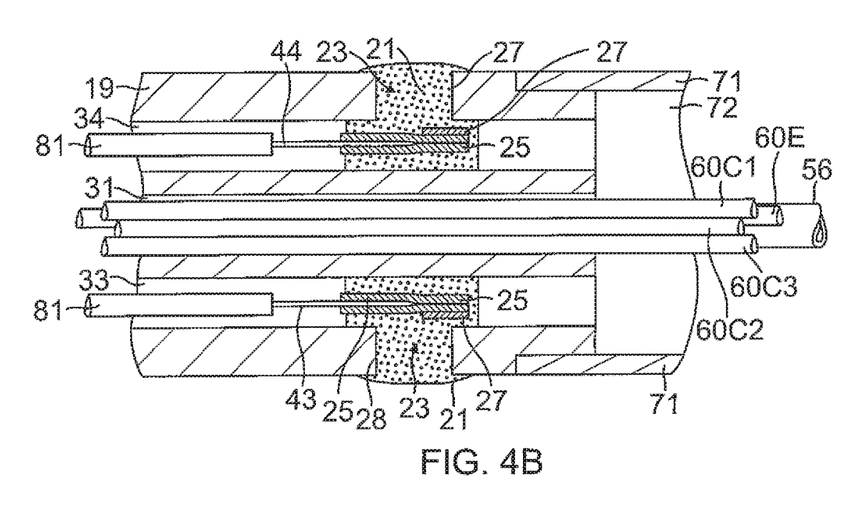
FIG. 4B is a side cross-sectional view of a junction between a deflectable intermediate section and a connector member, in accordance with one embodiment, taken along a second diameter generally perpendicular to the first diameter.

The puller wires are anchored at their distal ends to the sides of the tubing 19 of the intermediate section shaft 14, as shown in FIG. 4B. In this embodiment, a T-shaped anchor 23 is used for each puller wire. The anchor 23 comprises a short piece of tubular stainless steel 25, e.g., hypodermic stock, which is fitted over the distal end of each puller wire and crimped to fixedly secure it to the puller wire. The distal end of the tubular stainless steel 25 is fixedly attached, e.g., by welding, to a stainless steel cross-piece 27, such as stainless steel ribbon or the like. The cross-piece 27 sits in a notch 28 in a wall of the tubing 19. The stainless steel cross-piece 27 is larger than the notch 28 and, therefore, cannot be pulled through the notch. The portion of the notch 28 not filled by the cross-piece 27 is filled with glue 21 or the like, preferably a polyurethane glue, which is harder than the material of the tubing 19 of the intermediate section 14. Rough edges, if any, of the cross-piece 27 are polished to provide a smooth, continuous surface with the outer surface of the distal shaft 14.

Any other suitable technique for anchoring the puller wires in the intermediate section 14 can also be used. Alternatively, other means for deflecting the distal region can be provided, such as the deflection mechanism described in U.S. Pat. No. 5,537,686, the disclosure of which is incorporated herein by reference.

Longitudinal movement of the puller wires relative to the catheter body 12, which results in deflection of the intermediate section 14, is accomplished by suitable manipulation of a deflection control knob 17 on the control handle 16 (FIG. 1). Examples of suitable control handles manipulating a single puller wire for unidirectional deflection are disclosed, for example, in U.S. Pat. Nos. Re 34,502, 5,897,529 and 6,575,931, the entire disclosures of which are incorporated herein by reference. Suitable control handles manipulating at least two puller wires for bidirectional deflection are described in U.S. Pat. Nos. 6,123,699, 6,171,277, and 6,183,463, the disclosures of which are incorporated herein by reference.

Figure 3:
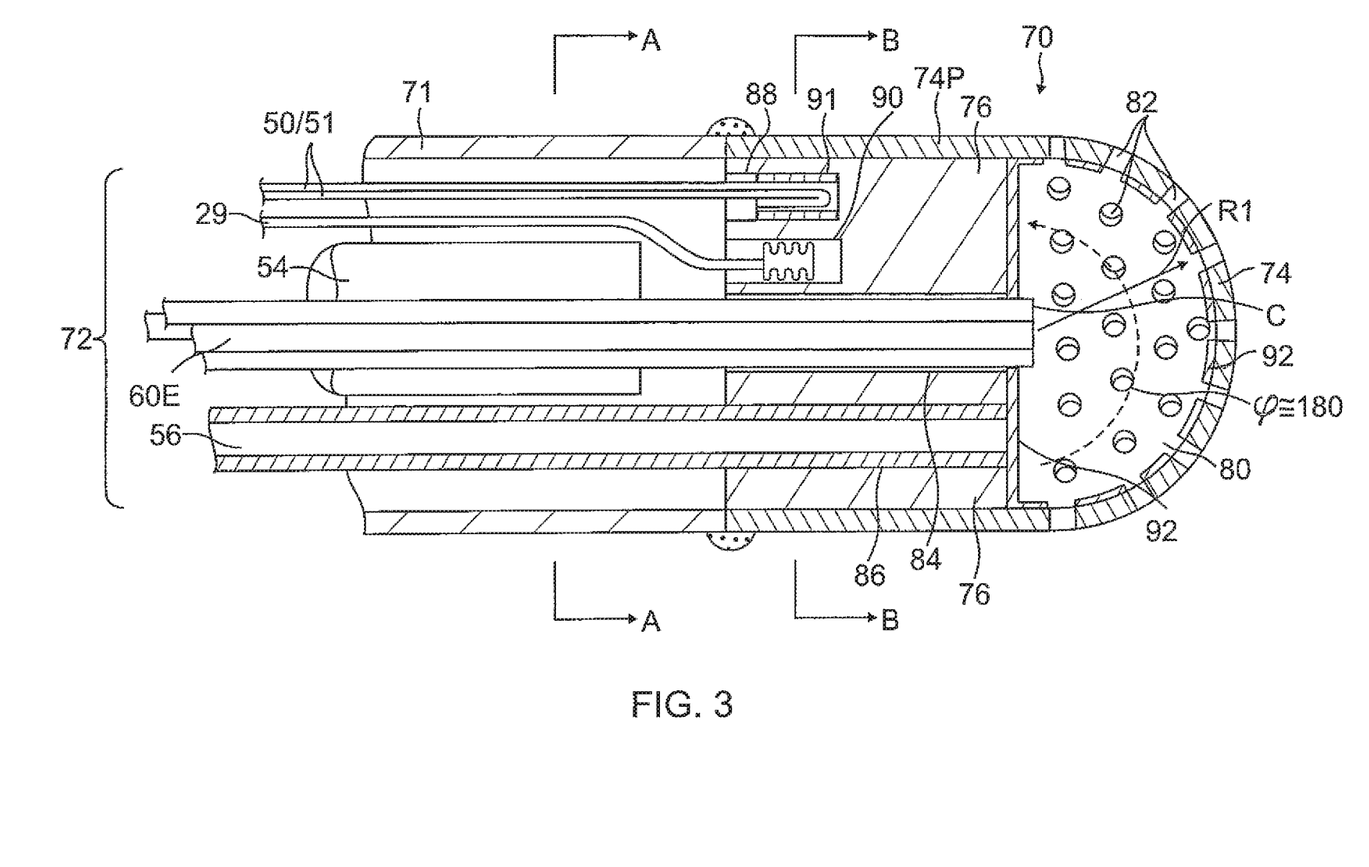
FIG. 3 is a side cross-sectional view of a distal section, including a connector member and a distal tip electrode of the present invention, in accordance with one embodiment.
Figure 3A:
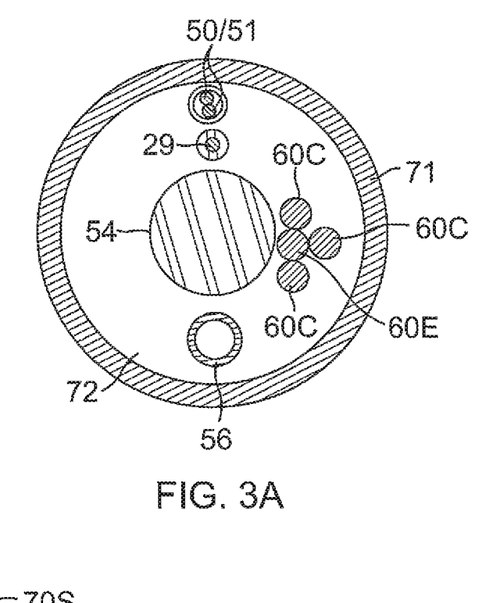
FIG. 3A is an end cross-sectional view of a connector member of FIG. 3, taken along line A-A.
Figure 3B:
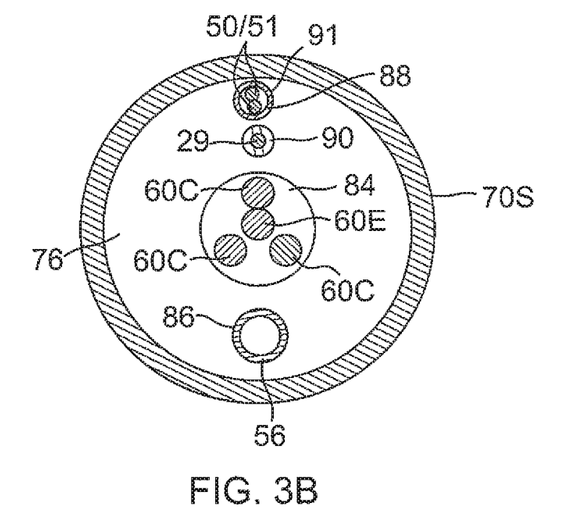
FIG. 3B is an end cross-sectional view of the distal tip electrode of FIG. 3, taken along line B-B.

As shown in FIGS. 3, 4A and 4B, distal of the intermediate section 14 is a distal section including a tip electrode 70 that is connected to the distal end of the tubing 19 by a connector tubing 71. The tubing 71 has a single center lumen 72 that allows components extending between the section 14 and the tip electrode 70 to reposition/realign as needed. The tubing 71 also houses an electromagnetic location sensor 54. The location sensor is used to determine the coordinates of the tip electrode in the patient's body. The corresponding sensor cable 52 extends from the control handle 16, through the lumen 18 of the catheter body 12, the lumen 30 of the intermediate section, and into the lumen 72 of the connector tubing 71. In the control handle 16, the sensor cable 52 is connected to a circuit board (not shown). Signals from the circuit board are transmitted to a computer and a monitor. The electromagnetic sensor 54 allows a physician to create a visual representation of the heart chamber and to view the location of the sensor, and therefore the catheter tip, within the chamber. The sensor cable 52 comprises multiple wires encased within a plastic covered sheath. The circuit board amplifies the signal received from the location sensor 54 and transmits it to the computer in a form understandable by the computer. Also, because the catheter is designed for single use only, the circuit board may contain an EPROM chip that shuts down the circuit board approximately twenty-four hours after the catheter has been used. This prevents the catheter, or at least the location sensor 54, from being used twice. A suitable control handle 16 is described in U.S. Pat. No. 6,024,739, the entire disclosure of which is incorporated herein by reference.

The location sensor 54 may comprise a magnetic-field-responsive coil, as described in U.S. Pat. No. 5,391,199. The plurality of coils enables the six-dimensional coordinates (i.e. the three positional and the three orientational coordinates) of the location sensor 77 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, International Publication Nos. WO 95/02995, WO 97/24983, and WO 98/29033, and U.S. patent application Ser. No. 09/882,125 filed Jun. 15, 2001, entitled "Position Sensor Having Core with High Permeability Material," the disclosures of which are incorporated herein by reference.

As shown in FIG. 3, the tip electrode 70 has a thin-walled shell member 74 and a plug member 76. The hollow shell member 74 has a distal portion defining a cavity or plenum chamber 80, and an open proximal tubular neck portion 74P which receives and is sealed by a disc-shaped the plug member 82.

The plug member 76 is formed with a center axial passage 84 to receive the optical waveguides 60E and 60C which extend through the passage 84 from the lumen 31 of the intermediate section 14, through the lumen 72 of the connector tubing 71, through the passage 84 and into the cavity 80. Distal ends of the optical waveguides are positioned at the center location C such that light delivered by the waveguides radiates outwardly throughout the cavity 80 from the center location C, as explained further below.

The plug member 76 also has an off-axis axial passage 86 for receiving the irrigation tubing 56 which extends from the lumen 35 of the intermediate section 14, through the lumen 72 of the connector tubing 71, and into the passage 86.

The plug member 76 on its proximal surface has a blind hole 88 which receives a distal end of the lead wire 29 for energizing the tip electrode 15. The plug member 76 also has a blind hole 90 on its proximal surface which receives distal ends of the thermocouple wires 50 and 51. The wires are provided for measuring the temperature of the tissue surrounding the tip electrode 15. Any conventional temperature sensor, e.g., a thermocouple or thermistor, may be used. In the depicted embodiment, the thermocouple is formed by an enameled wire pair. One wire of the wire pair is a copper wire 50, e.g., a 46 AWG copper wire. The other wire of the wire pair is a constantan wire 51, e.g., a 46 AWG constantan wire. The wires 50 and 51 of the wire pair are electrically isolated from each other except at their distal ends, where they are soldered together, covered with a short piece of plastic tubing 91, e.g., polyimide, and covered with polyurethane. The plastic tubing 91 is then glued or otherwise anchored in the blind hole 88.

Proximal of the control handle 16, the thermocouple wire pair 50 and 51 and the lead wire 29 are attached to an appropriate connector 79 (FIG. 1) connectable to a suitable temperature monitor. Within the catheter body 12 and the deflection control handle 16, the thermocouple wire 50 and 51 and the lead wire 29 may extend through a protective tube (not shown), which may be eliminated if desired. In an alternative embodiment, the copper wire 50 of the thermocouple can also be used as the lead wire for the tip electrode 15.

In accordance with a feature of the present invention, the shell member 74 of the tip electrode 15 has distal portion with a radially symmetrical configuration relative to the predetermined location in the cavity 80. That is, the portion of the shell member surrounding the cavity is uniformly spaced from the location by a distance R. In the illustrated embodiment of FIG. 3, the location is a center location C and the radially symmetrical configuration of the cavity is hemispherical as defined by a radius R1 for a radial angle Φ sweeping about 180 degrees. The present invention includes other configurations. In the illustrated embodiment of FIG. 5A, the radially symmetrical configuration is defined by a radius R2 for a radial angle Φ 1 sweeping up to about 360 degrees, or alternatively, a radial angle of Φ 2 sweeping up to about 270 degrees. Notably, for larger radial angles of Φ, the distal surface of the plug member 76 may be concave to follow the contour of a spherical cavity. In the illustrated embodiment of FIG. 5B, the radially symmetrical configuration is defined by a radius R3 for a radial angle Φ sweeping up to about 90 degrees. In accordance with a feature of the invention, where the connector tubing 71 has a diameter D, the radially symmetrical configuration of the shell member 74 may have a radius ranging between about D and 2D for radial angle Φ that sweeps up to about 90 to 360 degrees, and preferably up to about 180 to 270 degrees.

Figure 6:
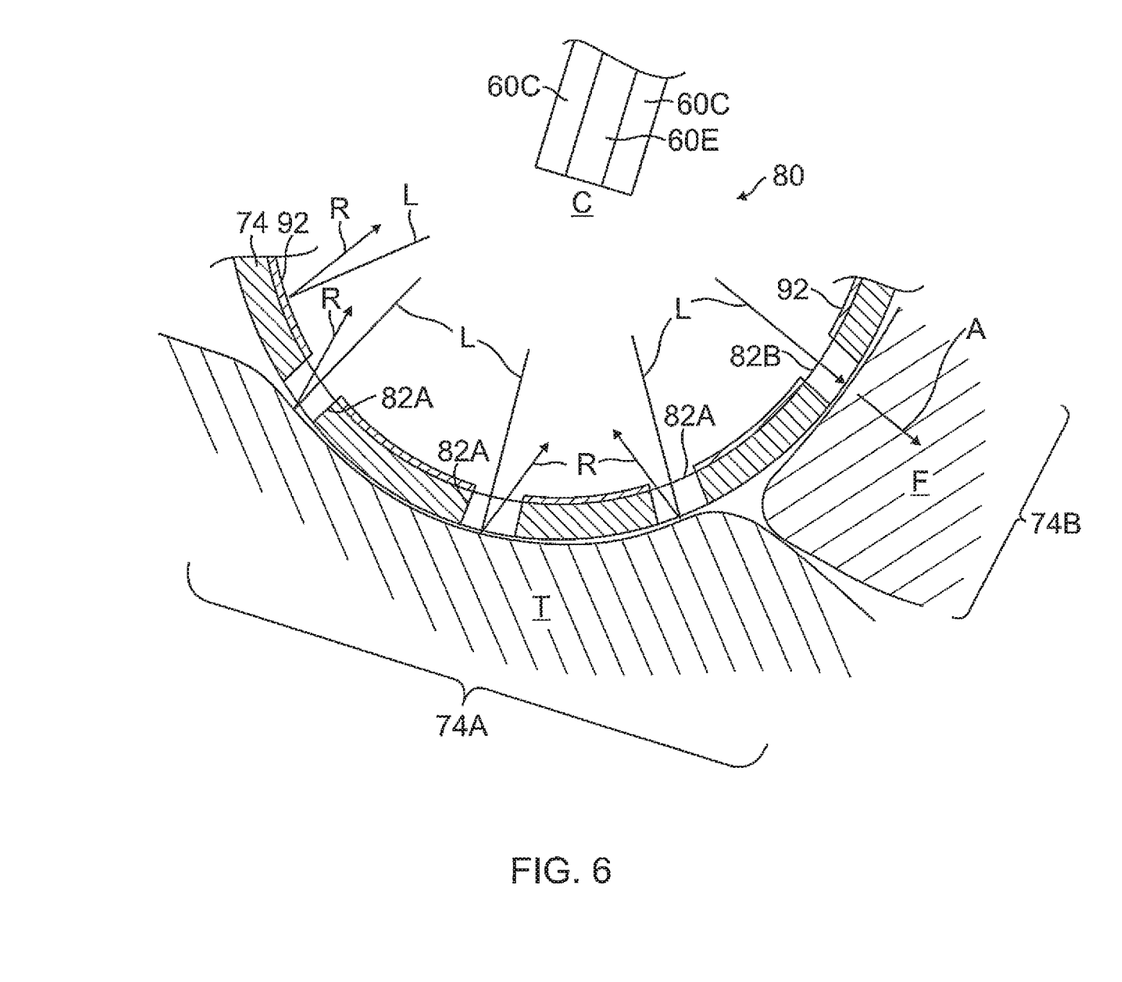
FIG. 6 is a detailed side cross-sectional view of a distal tip electrode in contact with tissue.

The emitter waveguide 60E delivering light into the tip electrode 15 and the collector waveguide(s) 60C collecting light in the cavity 80 extend generally alongside each other throughout the catheter. They may be bound to each other through the lumen 18 of the catheter body 12, the lumen 31 of the intermediate section 14, the lumen 72 of the connector tubing 71, and the passage 84 of the plug member 76. Light delivered to the tip electrode 15 by the waveguide 60E is emitted into the cavity 80 from the center location C and radiates outwardly toward the shell member 74. The distal portion of the shell member 74 surrounding the cavity 80 is formed with a plurality of apertures 82 and inner surfaces of the distal portion of the shell member 74 surrounding the cavity 80 and of a distal surface of the plug member are coated with a reflective coating 92. As illustrated in FIG. 6, for any portion 74A of the shell member 74 in contact with tissue, apertures 82A in that portion are covered by tissue T. For any portion 74B of the shell member 74 out of contact with tissue, apertures 82B in that portion are covered by fluid F, such as blood. Accordingly, the light entering the cavity 80 from the distal end of the emitter waveguide 60E can either strike the coating 92 inside the cavity and be reflected, or it can pass through the apertures 82 where it interacts either with surrounding tissue T which interacts with the light in one manner, or with fluid F, such as blood, which interacts with the light in another manner. Thus, a difference or change in one or more detectable characteristics or parameters of the light present in the cavity 80 having interacted with either tissue T or fluid F (or any other matter) as collected by the collector waveguides compared to the light in the cavity as originally emitted by the emitter waveguide should provide an indication as to how much of the light interacted with tissue and how much of the light interacted with fluid. Such an indication can provide further indications, including the number of apertures and the amount or percentage of surface of the shell member surrounding the cavity 80 that is surrounded by or in contact with tissue versus fluid. It is understood that the one or more detectable parameters include amount, intensity or fluorescence. For example, where the detectable parameter is amount or intensity of light, and it is understood that tissue generally reflects light whereas fluid generally absorbs light, the more equal the intensity of light present in the cavity (as collected by the collecting waveguides) is to the intensity of light in the cavity as originally emitted by the emitting waveguide, then presumably the lesser the number of apertures 82 that are covered by light-absorbing fluid, and thus the more the outer surface of the shell member is presumably in contact with tissue for better lesions during ablation. Thus, by analyzing the amount or intensity of light collected in the cavity, for example, by determining a ratio of light reflected versus light absorbed, a determination of how much of the portion of the shell member surrounding the cavity is in contact with tissue.

For example, where the detectable parameter is fluorescence, and it is understood that tissue and blood have different fluorescence properties at different wavelengths, the differences between the wavelength of light emitted versus the wavelengths of the light collected help determine what ratio of the tip electrode is contacting tissue versus blood.

Figure 5A:
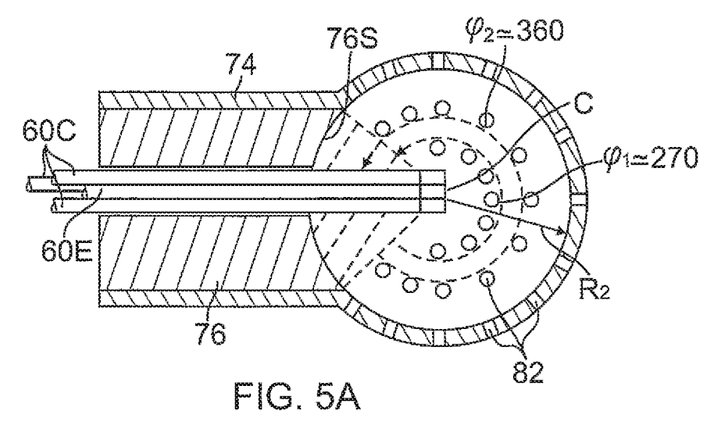
FIGS. 5A-5D are side cross-sectional views of a distal tip electrode in accordance with alternate embodiments of the present invention.
Figure 5B:
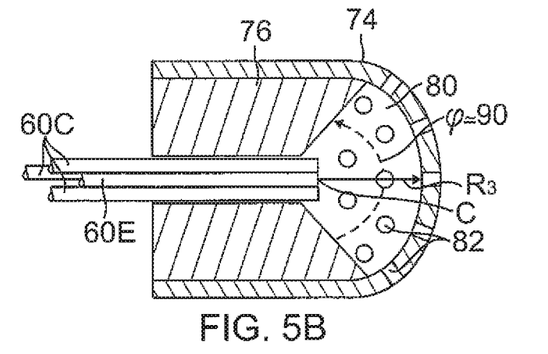
Figure 5C:
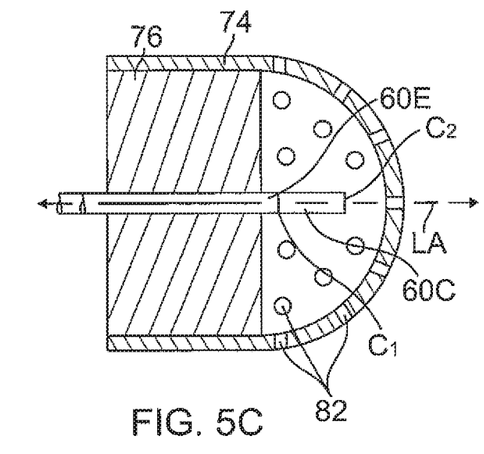
Figure 5D:
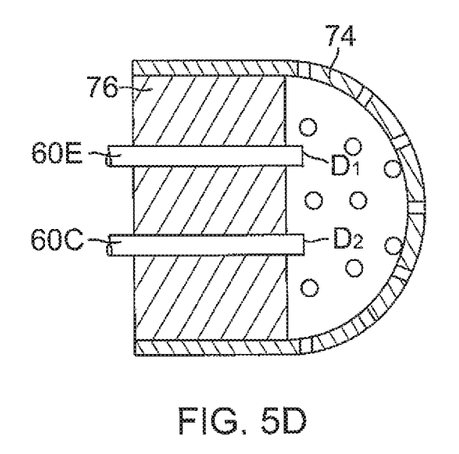

In the illustrated embodiment of FIGS. 3, 5A and 5B, the distal ends of both the emitter waveguide 60E and the collector waveguides 60C are positioned generally at the center location C so that the location from where the light radiates outwardly is generally identical to the location where reflected light is collected in the cavity 80. However, it is understood that the either or both of the distal ends of the emitter and collector waveguides may be positioned elsewhere in the cavity 80. For example, the distal ends of the emitter and collector waveguides may be positioned at different predetermined locations from each other, with one being at the center location and the other(s) at another location C2 along a center longitudinal axis LA of the tip electrode. Alternatively, the distal ends of one or more emitter and collector waveguides may be positioned at one or more off-axis locations D1 and D2 (FIG. 5D). In fact, the distal ends of the waveguides may be positioned at any suitable location(s) in the cavity, although such arrangements may require more involved analyses relative to the geometry of the cavity, but the data collected would nevertheless provide an indication of the interaction of light and the matter(s) surrounding the tip electrode, including how much contact the shell member has with tissue versus fluid.

It is understood that the total plurality of emitter and collector waveguides may vary depending on desire and need. Moreover, the plurality of emitter waveguide(s) and the plurality of collector wave guide(s) can be equal or unequal to each other. For example, the plurality of each may range between about one and three, including one center emitter wave guide and two adjacent collector wave guides, or any other combinations.

Figure 7A:
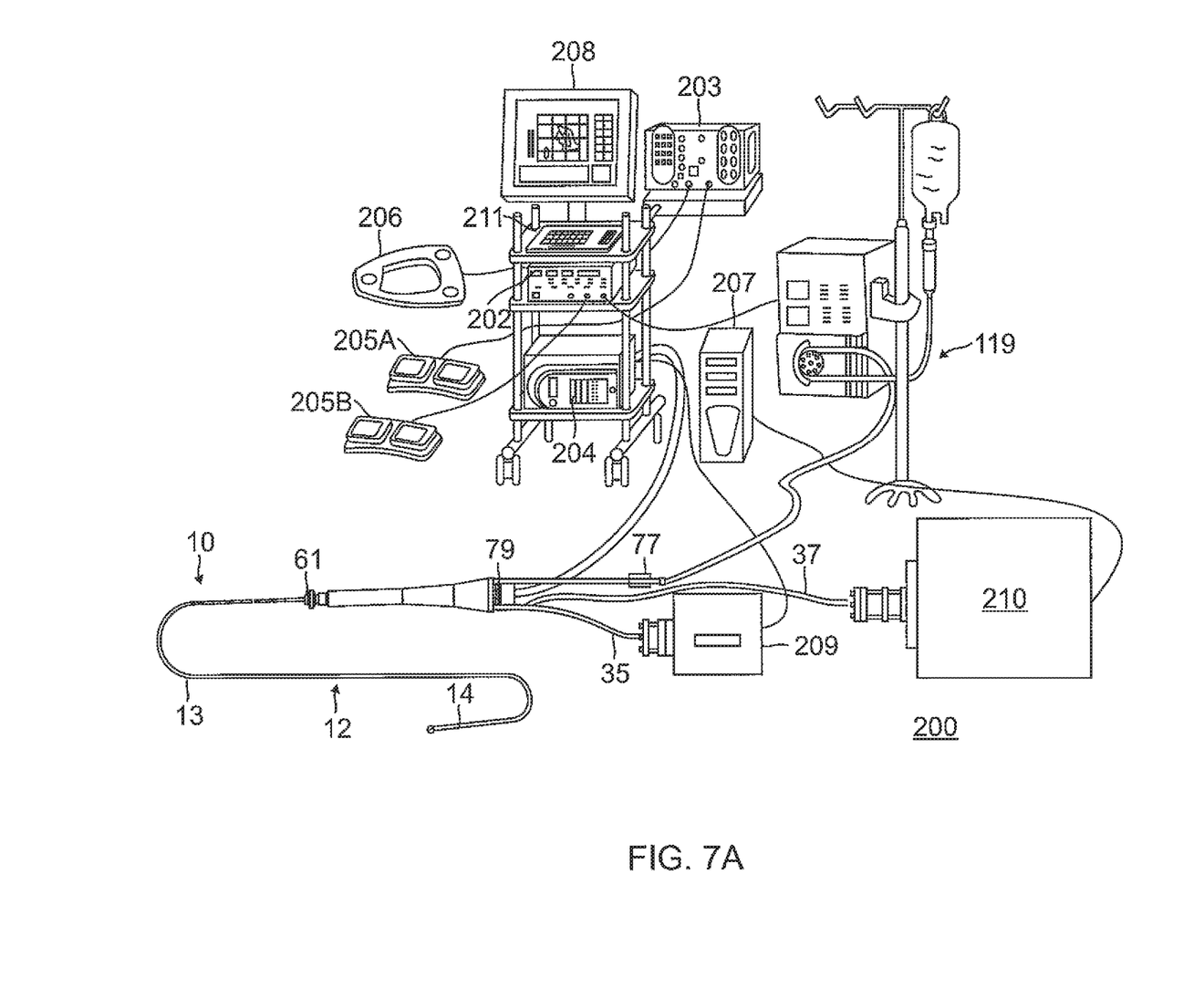
FIG. 7A is a schematic diagram of a system of the present invention, in accordance to one embodiment.

Proximal of the deflection control handle 16, a proximal end of the irrigation tubing 56 is connected to a luer connector 77, which is connected to an irrigation pump or other suitable fluid infusion source 119, as shown in FIG. 7A). In the control handle 16, the electrode lead wire 29 and the thermocouple wires 50 and 51 are connected to a suitable connector 79, such as a 10-pin electrical connector, for connecting the electrode lead wire to a source of ablation energy and the thermocouple wires to a suitable monitoring system. The emitter wave guide 60E extends out of the proximal end of the control handle 16 and into a protective sheath 35, as shown in FIG. 7A, for communication with a suitable light source, for example, a lamp or multiple lasers. The collector wave guide(s) 60C extend out of the proximal end of the control handle 16 and into a protective sheath 37, as shown in FIG. 7A, for communication with a suitable light analyzer, e.g., a spectrometer, to process the collected light.

Figure 7B:
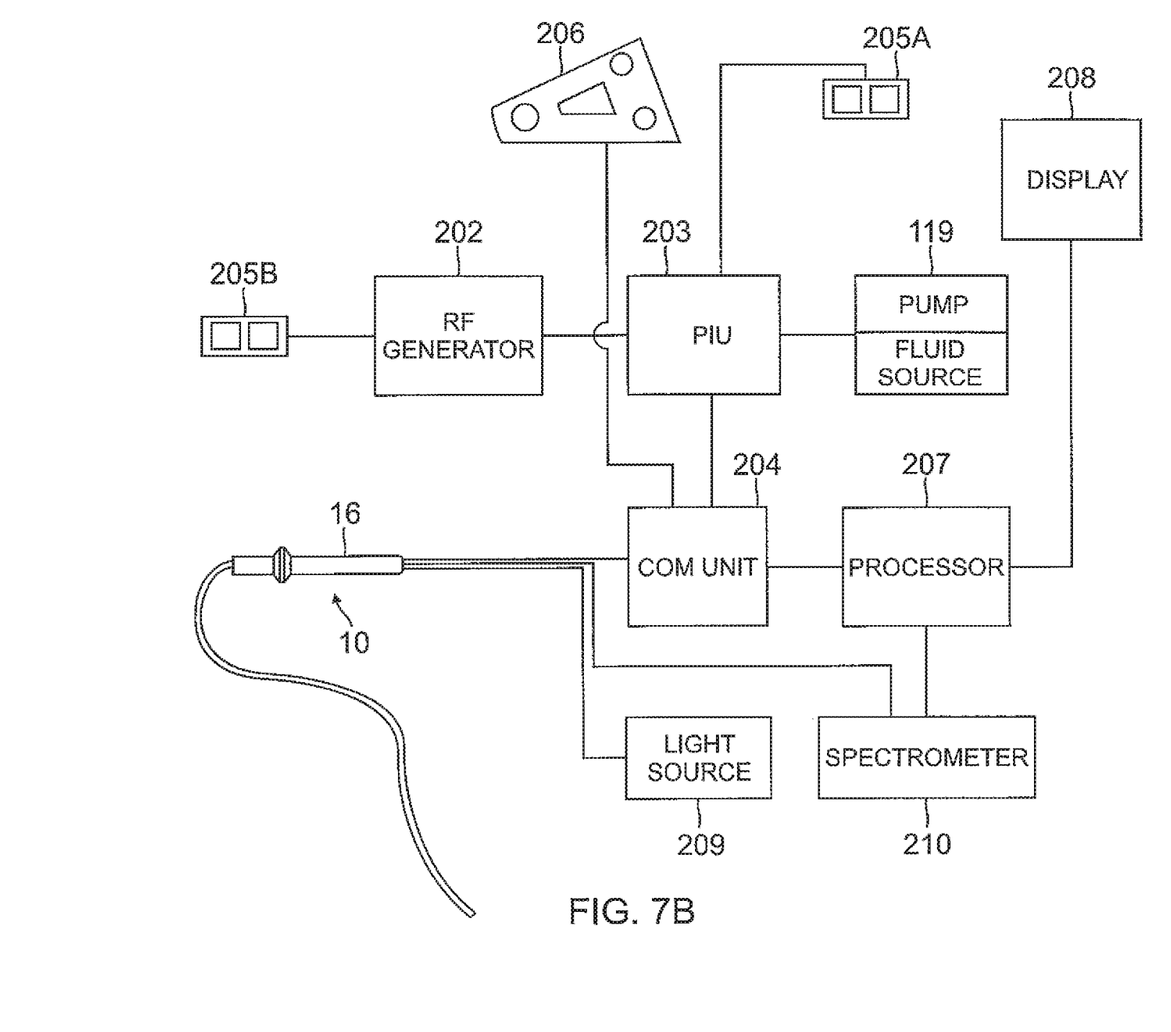
FIG. 7B is a block diagram of the system of FIG. 7A.

As shown in FIGS. 7A and 7B, the catheter 10 may be used with an integrated ablation and spectroscopy system 200. In the illustrated embodiment, the system includes an RF generator 202, a patient interface unit 203, a communication (COM) unit 204, a location pad 206, a processor 207, input device (e.g., keyboard) 211, and a display 208. The COM unit 204 provides electronics for ECG, electrogram collection, amplification, filtering and real-time tracing of catheter distal tip. The PIU 203 allows communication with various components of the system 200, including signal generator, recording devices, etc. The location pad 206 includes magnetic field generators (e.g., coils) and is typically positioned under a patient's body to generate magnetic fields within the patient's body. Responsive to these magnetic fields, the location sensor 54 housed in the distal end of the catheter generates electrical signals which are received by the PIU 203 and transmitted to the COM unit 204 and processed by the processor 207 in order to determine the position (location and/or orientation) coordinates of the catheter distal end. The processor 207 uses the coordinates in driving the display 208 to show location and status of the catheter. Other signals from the catheter 10, for example, tissue electrical activity and temperature, are also transmitted to the COM unit 204 and the processor 207 via the PIU 203 for processing and analysis, including 3-D mapping of the patient's heart that is shown on the display 208. This method of position sensing and processing is described in detail, for example, in PCT International Publication WO 96/05768, whose entire disclosure is incorporated herein by reference, and is implemented in the CARTO system produced by Biosense Webster Inc. (Diamond Bar, Calif.).

For ablation, the RF generator 202 supplies RF ablation energy to the tip electrode 15 of the catheter 10 via the PIU 203. For spectroscopy, the system 200 further includes a light source 209 which provides incidental light energy to the catheter 10 via the emitter wave guide 60E. Light collected by collector wave guides 60C are transmitted to a spectrometer 210 which provides representative signals to the processor 207 which processes the signals to determine various parameters and/or characteristics of the target issue illuminated. The system may include a first foot pedal 205A connected to the PIU 203 to be used for acquiring catheter location points and a second food pedal 205B connected to the RF generator 202 for activating/deactivating the RF generator 202.

To use a catheter of the invention, an electrophysiologist may introduce a guiding sheath and dilator into the patient, as is generally known in the art. A guidewire may also be introduced for a catheter adapted for such use. For example, the catheter may be introduced to the right atrium (RA) via the inferior vena cava (IVC). To reach the left atrium (LA), the catheter passes through the septum. Through the guiding sheath, the length of the catheter can be passed through the patient's vasculature to the desired location. Once the distal end of the catheter reaches the desired location, e.g., the right atrium RA, the guiding sheath is withdrawn to expose the tip electrode 15 and the intermediate section 14. The control handle 16 may be manipulated as needed to deflect the intermediate section 14 into position. After the distal end of the catheter body 12 is positioned on and in contact with a target tissue, light is transmitted by the emitter wave guide 60E into the cavity 80 of the tip electrode 15. As shown in FIG. 6, the light radiates outwardly from a first predetermined position in the cavity toward the shell member 74 where either it strikes the reflective coating 92 and is redirected within the cavity or it passes through the apertures 82 to outside the cavity where it interacts with tissue T in one manner or with fluid F in another manner, where such interactions affect and/or alter one or more characteristics or parameters of the light. Light so affected or altered is collected by the collector wave guides 60C and transmitted proximally through the catheter to the spectrometer for analysis. Depending on the analysis, selected action(s) may be taken, including energizing the tip electrode for ablation where the indication is that the tip electrode has sufficient contact with tissue.

RF energy may be applied to the tip electrode 15 for ablation. Irrigation fluid may also be provided to tip electrode during ablation via the fluid source and pump 119 that provides the transported through the irrigating tubing 56. Fluid enters the cavity via the irrigation tubing 56 and exits the cavity via the apertures 82.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be adapted to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body;
    a distal tip electrode having a shell defining a hollow cavity, and a plug member, the shell having one or more apertures and an inner surface having a reflective coating;
    at least one emitter optical waveguide extending through the catheter body and the plug member and having a distal emitter end extending partially into the hollow cavity, the at least one emitter optical waveguide configured to deliver light into the hollow cavity, where at least a first portion of the light exits the one or more apertures; and
    at least one collector optical waveguide extending through the catheter body and plug member and having a distal collector end extending partially into the hollow cavity, the at least one collector optical waveguide configured to collect light,
    in which the distal emitter end and the distal collector end are generally coterminous within the hollow cavity, and the shell and the plug member define a radially symmetric configuration of the hollow cavity that is radially symmetric about the distal emitter end.

2. The catheter of claim 1, in which the radially symmetric configuration is radially symmetric about a center location in the hollow cavity.

3. The catheter of claim 1, in which the radially symmetrical configuration of the hollow cavity is a hemispherical configuration.

4. The catheter of claim 3, in which the hemispherical configuration is defined by an angle $\Phi$ of about 180 degrees from a first point on a distal surface of the plug member sweeping around the inner surface of the shell to a second point of the surface of the plug member.

5. The catheter of claim 1, in which the radially symmetrical configuration is defined by an angle $\Phi$ of up to about 360 degrees from a first point on a distal surface of the plug member sweeping around the inner surface of the shell to a second point on the distal surface of the plug member.

6. The catheter of claim 1, in which the radially symmetrical configuration is defined by an angle $\Phi$ of up to about 270 degrees from a first point on a distal surface of the plug member sweeping around the inner surface of the shell to a second point on the surface of the plug member.

7. The catheter of claim 1, in which a distal surface of the plug member has a concavity.

8. The catheter of claim 1, in which the emitter optical waveguide is adapted to emit light of a first intensity and the collector optical waveguide is adapted to collect light of a second intensity.

9. The catheter of claim 1, in which the emitter optical waveguide is adapted to emit light of a first wavelength and the collector optical waveguide is adapted to collect light of a second wavelength.

10. A system for ablation and spectroscopy, comprising:
    the catheter of claim 1;
    an RF generator adapted to provide RF energy to the distal tip electrode;
    a light source adapted to provide the light; and
    a spectrometer adapted to analyze the light collected by the at least one collector optical waveguide.

11. The system of claim 10, further comprising:
    a patient interface unit;
    a communication unit;
    a processor; and
    a display,
    in which the patient interface unit is adapted to send and receive signals from the RF generator and the communication unit, in which the communication unit is adapted to send and receive signals from the patient interface unit, in which the processor is adapted to send and receive signals from the communication unit, and in which the display is adapted to receive signals from the processor.

12. A catheter comprising:

an elongated catheter body;

a distal tip electrode having a plug member and a shell defining a hollow cavity, the shell having one or more apertures and an inner surface having a reflective coating, and the shell and plug member defining a radially-symmetrical configuration;

at least one emitter optical waveguide extending through the catheter body and the plug member and having a distal emitter end positioned in a center location in the hollow cavity such that the radially-symmetrical configuration is radially symmetrical about the distal emitter end, the at least one emitter optical waveguide configured to deliver light into the hollow cavity, where at least a first portion of the light exits the one or more apertures; and at least one collector optical waveguide extending through the catheter body and having a distal collector end positioned in the hollow cavity, the at least one collector optical waveguide configured to collect light, in which the distal emitter end and the distal collector end are generally coterminous within the hollow cavity.

13. The catheter of claim 12, in which the radially symmetrical configuration of the cavity is a hemispherical configuration.

14. The catheter of claim 13, in which the hemispherical configuration is defined by an angle Φ of about 180 degrees from a first point on a distal surface of the plug member sweeping around the inner surface of the shell to a second point of the surface of the plug member.

15. The catheter of claim 12, in which the radially symmetrical configuration is defined by an angle Φ of up to about 360 degrees from a first point on a distal surface of the plug member sweeping around the inner surface of the shell to a second point on the distal surface of the plug member.

16. The catheter of claim 12, in which the radially symmetrical configuration is defined by an angle Φ of up to about 270 degrees from a first point on a distal surface of the plug member sweeping around the inner surface of the shell to a second point on the surface of the plug member.

17. A system for ablation and spectroscopy, comprising:

the catheter of claim 13;

an RF generator adapted to provide RF energy to the distal tip electrode;

a light source adapted to provide the light; and a spectrometer adapted to analyze the light collected by the at least one collector optical waveguide.

* * * * *